United States Patent [19]

Melin et al.

[11] 4,346,968

[45] Aug. 31, 1982

[54] WALL MOUNTED VISUAL FIELD TESTING SYSTEM

[75] Inventors: John A. Melin, Oakland; Russell P. Irwin, Berkeley; Gordon L. Epstein, San Francisco, all of Calif.

[73] Assignee: Pacific Innovations, San Bruno, Calif.

[21] Appl. No.: 118,566

[22] Filed: Feb. 4, 1980

[51] Int. Cl.³ .............................................. A61B 3/02
[52] U.S. Cl. ........................................ 351/23; 351/36
[58] Field of Search ............................. 351/23, 24, 36

[56] References Cited

U.S. PATENT DOCUMENTS

| | | |
|---|---|---|
| 3,025,755 | 3/1962 | Koetting . |
| 3,718,386 | 2/1973 | Lynn et al. ....................... 351/23 X |
| 3,837,734 | 9/1974 | Regan ................................... 351/17 |
| 3,982,828 | 9/1976 | Woolf .................................... 351/23 |
| 4,063,807 | 12/1977 | Gelius et al. ........................... 351/23 |

OTHER PUBLICATIONS

Cohn et al., The Diodewand, Amer. Journ. of Optometry & Psy. Optics, vol. 51, No. 12, Dec. 1974.

Primary Examiner—John K. Corbin
Assistant Examiner—Rodney B. Bovernick
Attorney, Agent, or Firm—Majestic, Gallagher, Parsons & Siebert

[57] ABSTRACT

A visual field testing unit having a thin, light-weight screen adapted for mounting on an inside building wall and having a plurality of individually energizable substantially point light sources across its surface but behind a semi-transparent screen so that the lights are not visible from the outside until lit. A hand-held control unit allows a practitioner to test the visual field of a patient sitting a distance from the wall that carries the screen. The practitioner sequences various light patterns according to automatic preprogrammed patterns and duration of energization.

10 Claims, 4 Drawing Figures

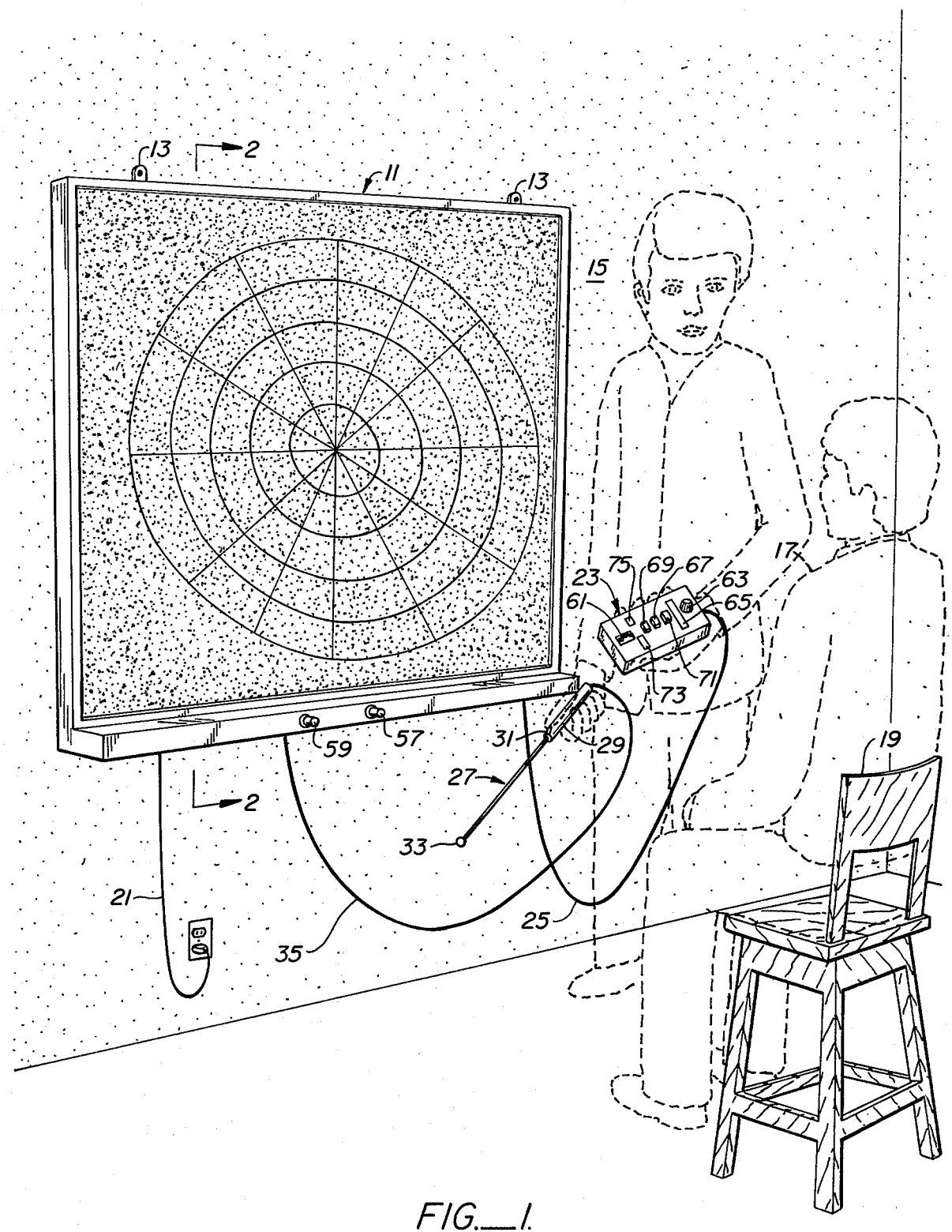
FIG._1.

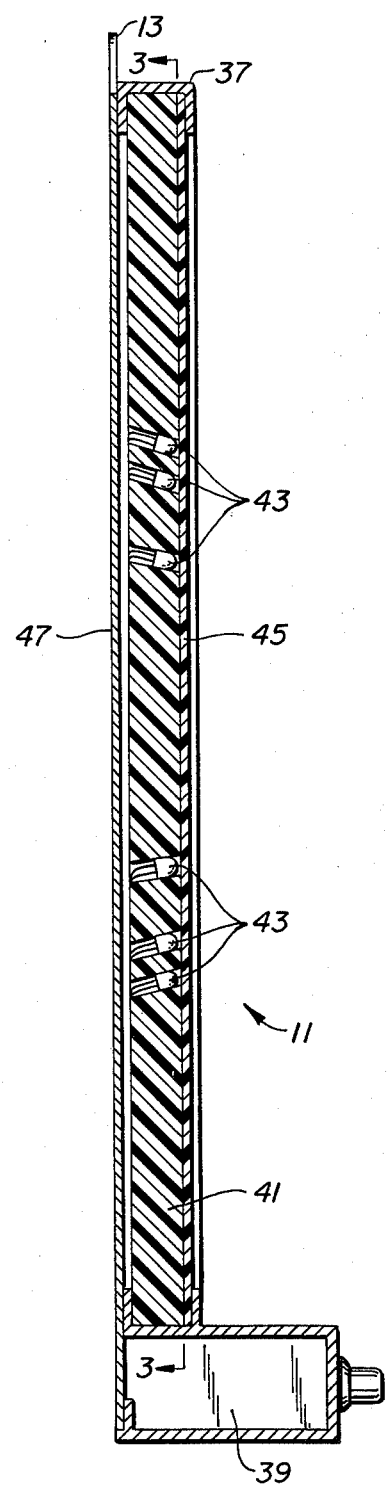
FIG._2.

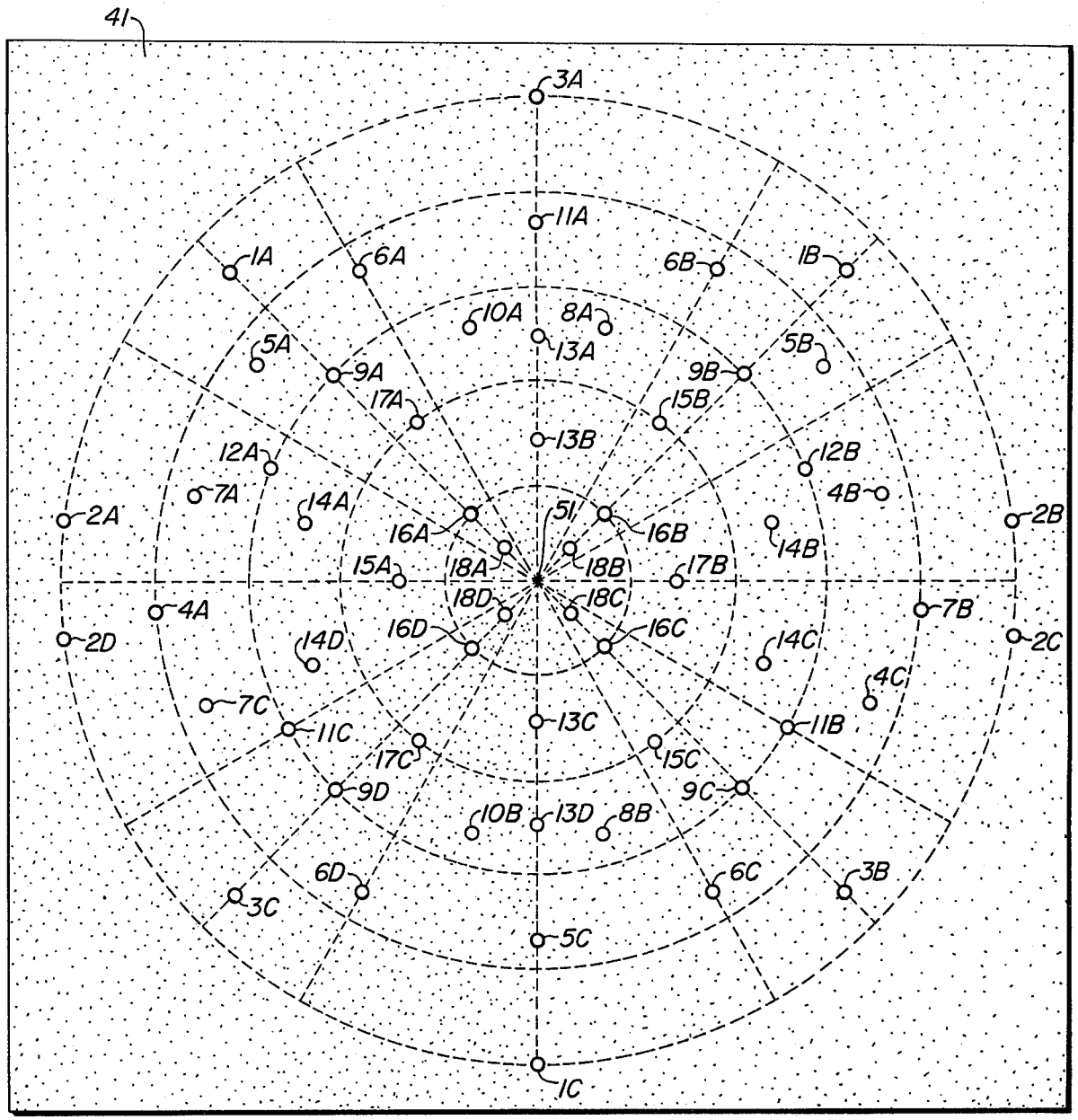
FIG._3.

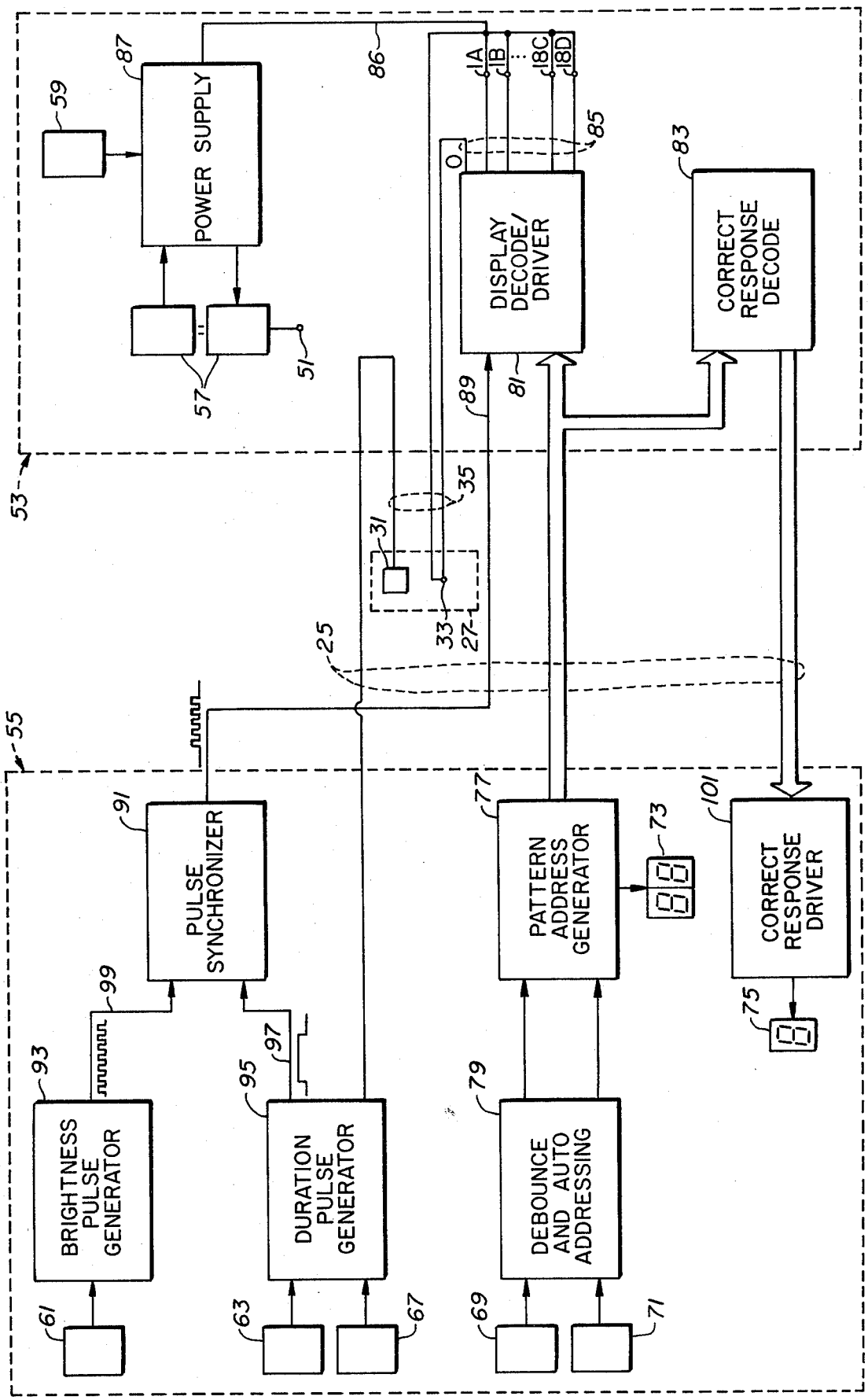
FIG._4.

4,346,968

WALL MOUNTED VISUAL FIELD TESTING SYSTEM

BACKGROUND OF THE INVENTION

This invention relates generally to human eye testing devices, and more particularly to those types of devices that are especially adapted to test the visual field of humans.

Many visual field testing devices have been marketed or proposed in the literature. Four such devices are disclosed in the following U.S. Pat. Nos. 3,025,755—Koetting (1962); 3,837,734—Regan (1974); 3,982,828—Woolf (1976); and 4,063,807—Gelius et al (1977). Commercially available equipment predominantly tends to be highly automatic, expensive, uncomfortable for the patient and beyond the ability for an opthalmologist or other practitioner to make sure the test is proceeding as desired.

Therefore, it is the principal object of the present invention to provide a visual field testing device that is economical, convenient and quick to use yet is also reliable and enables accurate diagnosis of any visual field problems, thereby increasing the frequency of a visual field testing of patients by private practitioners and thus improving eye care.

SUMMARY OF THE INVENTION

This and additional objects are accomplished by the various aspects of the present invention wherein, briefly, a plurality of substantially point light sources are positioned across a two-dimensional surface that is made a part of a thin screen constructed from lightweight materials for hanging on a wall. This light mounting surface is covered by a semitransparent tinted sheet that hides the light from view except when they are energized. A hand-held control unit permits the doctor or other practitioner to stand adjacent the screen and face the patient who is sitting a distance from the wall upon which the screen is hung. This configuration allows the practitioner to observe where the patient is looking during the test, the patient being instructed to fix his eyes on a center target light that remains lit all the time.

The control unit maintains an electronic memory of a number of distinct light patterns that are to be created by various combinations of the individual lights. The patient is exposed to these various light patterns one at a time as the operator initiates the automatic sequencing control between tests. The duration that a given pattern is displayed, plus the brightness of that display, are accurately controllable by the practitioner to allow complete diagnosis of any suspected patient blind spots. After a pattern of lights has been displayed, the control system gives an indication of the number of lights which the patient should have seen which can then be compared with what the patient says that he or she did see. The practitioner need not look at the screen during the test but is told how many lights the patient should be seeing while the practitioner is facing the patient. An optimum balance is provided between automatic control and practitioner control of the testing sequence so that the best possible results of the visual field extent of the patient can be determined.

Additional objects, advantages and features of the various aspects of the present invention will be best understood from a review of the following description of a detailed embodiment, which description should be taken in conjunction with the accompanying drawings.

BRIEF DESCRIPTION OF THE DRAWINGS

FIG. 1 illustrates the major components of the visual field tester according to the present invention and how it is used with a patient;

FIG. 2 is a cross-sectional view of the wall screen portion of the visual field tester of FIG. 1 taken at Section 2—2 thereof;

FIG. 3 is a front view of the wall panel of the visual field tester of FIG. 1 as viewed from Section 3—3 of FIG. 2; and FIG. 4 is a schematic block diagram showing the electronic control circuitry of the visual field testing system of FIGS. 1 through 3.

DESCRIPTION OF A PREFERRED EMBODIMENT

Referring initially to FIG. 1 the main components of the visual field testing unit according to the present invention are illustrated. A visual field testing board 11 is mounted by appropriate conventional brackets 13 to a wall 15 on an interior of a building, such as in an opthalmologist's or other practitioner's office. In a specific form the wall mounted panel 11 is about one meter square. A patient, illustrated as 17, sits on a chair 19 facing the panel 11 with his or her eyes spaced about 1 meter away from the front of the panel 11. By keeping the two-dimensional extent of the light patterns about the same as the distance that the patient is placed from the panel, conventional peripheral and other field tests can be performed. The patient is preferably positioned sideways and in height relative to the panel 11 so that his or her eyes are directly opposite a center of the panel 11. This can be accomplished for different size patients by an elaborate mounting mechanism for the panel 11 or, preferably, by a chair that is movable with respect to the panel 11, especially in a vertical direction.

Before describing the panel 11 in greater detail with respect to other figures, it will be noted from FIG. 1 that a standard power cord 21 is provided from the panel 11. A hand control unit 23 is connected by a cable 25 to the panel 11 and permits an opthalmologist or other practitioner to control the test from a position remote from the panel 11 by operating the controls and observing the visual indicators provided as part of the hand control unit. It particularly allows the practitioner to stand adjacent the wall 15 along the side the panel 11 so that the practitioner can make sure that the test results are given by the patient 17 when the patient is actually fixing his or her eyes on a center of the panel 11. The purpose of the device shown in the drawings is to check field vision of the patient and this can only be done with any certainty if it is known that the patient is fixing his or her stare to a known position within the middle of the panel 11. Also provided is a light wand 27 having a handle 29, a push button test switch 31 and a light source of very small dimensions, such as a light emitting diode 33. The switch 31 and light 33 at the end of the wand 27 are connected with the panel 11 through a cable 35.

Referring to FIGS. 2 and 3, in addition to FIG. 1, the construction of the panel 11 will be explained in more detail. A frame 37 is made of a lightweight but rigid material, preferably aluminum. At the bottom of the panel 11 is formed a compartment 39 as part of the frame 37 within which various electronic components are placed for operating and controlling the vision testing device. Mounted within the frame 37 is a panel 41 of lightweight material, preferably plastic foam filler, in which a plurality of light emitting diodes 43 are embedded. The light emitting diodes 43 are positioned so that their light emitting surfaces are facing frontwards against a semi-transparent sheet 45 which forms the front surface of the panel 11. An opaque back cover 47 is provided on the rear of the panel 11 and is the surface which contacts a wall upon which the panel 11 is principally designed to be mounted. The semi-transparent panel 45 is preferably made of a lightweight plastic material, but could also be glass, that is heavily tinted so that the light emitting diodes 43 are not visible from the room by the patient unless the lights 43 are energized in a manner to be lighted. The front surface of the screen 45 is preferably a black matte finish in order to prevent reflections from room lighting that would interfere with the conducting of the test.

The positioning of the lights 43 across the panel 11 is illustrated in FIG. 3. There are 18 different light patterns illustrated in this specific example. The notation of the lights, each of which is indicated by a small circle of FIG. 3, is that those that form a part of a given pattern are identified with the same number followed by a distinct letter. For example, there are three lights forming a pattern 5, a light 5A in the upper left quadrant, a light 5B in the upper right quadrant and a light 5C in a lower portion of the panel 11. When an opthalmologist or practitioner is using this device and wants to test whether a patient can see all three lights of the pattern 5, then these three lights are energized at the same time while all other lights remain off. Similarly, a pattern 6 has four lights, 6A, 6B, 6C and 6D, one in each of the four quadrants of the pattern of FIG. 3. All four lights in the pattern 6 are similarly energized at one time to test a patient's ability to see the lights in these positions while all other lights remain off. This is the case with all 18 patterns, each of which has either two, three or four lights as part of the pattern. No light in this example forms a part of more than one pattern. Throughout the use of this device a center light 51 remains lit and the patient is instructed to look with one eye at that center light 51 during the examination. The examination with the specific device being described herein constitutes a time sequential lighting of the various light patterns 1 through 18.

Referring to FIG. 4, a block diagram of the electronic driving and control circuitry for the panel of FIGS. 1-3 is illustrated. A portion of the circuit of FIG. 4 within the dotted outline 53 is physically positioned within the chassis 39 of the display panel 11. Another portion of the circuitry of FIG. 4 within the dotted outline 55 is physically located within the hand control unit 23. On the bottom of the display board 11 is a control 57 which forms a power on/off switch and a potentiometer which controls the brightness of the center light 51. A second control 59 controls the overall brightness of the pattern light emitting diodes.

As part of the hand control unit 23, a second brightness control knob 61 is provided with 16 discreet positions for controlling the brightness of the lights within the patterns 1 through 18. In a given installation, the overall brightness control 59 on the panel 11 is turned so that the pattern lights are barely visible given the particular general illumination in a room where it is installed, while the switch 61 is placed in its least bright position. The opthalmologist or other practitioner can then increase the brightness as desired during an examination by turning the knob 61.

Also on the hand control unit 23 is a duration selection control 63. This control permits the practitioner to select one of several given time periods that the pattern lights will remain lit once they are initiated. Thus, it is not up to the operator to turn the pattern lights off when he or she thinks a certain time has elapsed, but rather the electronic circuitry of FIG. 4 provides for them to go off automatically after a certain time period that is selected by the operator through the knob 63. In the specific example being described, these time durations are 0.25 second, 0.50 second and 1.0 second, in addition to a position for continuous lighting. The duration control setting is shown in a display 65 on the hand control unit 23 adjacent the knob 63. The display 65 may be, for example, a mechanical wheel attached to the knob 63. The duration and brightness controls of the hand control unit allow the practitioner to adjust the test individually for each patient but still retaining automatic features of the test that make it simple and rapid to execute. Also, it permits variation for a single patient where the practitioner denotes a potential problem from the number of lights the patient indicates he or she sees in a given pattern. If a light is missed, the practitioner can then go back to alter the duration, brightness or both to determine the extent of the patient disability to see one more lights of a given light pattern.

The electronic control circuitry of FIG. 4 is designed to automatically sequence through the 18 different light patterns one at a time, under the control of the practitioner through the hand control unit 23. The light patterns are energized in numerical sequence. The practitioner initiates the lighting of a given pattern for conducting a test by pushing a switch push button 67. The particular pattern upon which the control electronics is set at that instant will then be lighted for the time period set by the duration control 63. The operator may then advance to the next light pattern by pushing a pattern increment push button switch 69 or may return to the next preceding pattern by pushing a pattern decrement push button switch 71. In either event, no lights will be lit until again the operator pushes the test button 67 to initiate such lighting.

The specific operation of the unit becomes clearer to understand when the electronic block diagram of FIG. 4 is reviewed. Central to the circuitry for determining which of the 18 light patterns is to be energized is a pattern address generator 77 which contains as its principal component a ring counter with, for this very specific example, 0-18 counts possible. Circuitry is also provided (not shown) to make sure that the counter starts at the position "0" when the power to the testing device is first turned on. From then on, the counter is incremented in response to the button 69 being pushed and decremented in response to the button 71 being pushed. Both of the buttons 69 and 71 are connected to the counter within the generator 77 through intermediate circuitry 79 which has two functions. The first function of the circuitry 79 is to compensate for the mechanical vibration of the push button switches 69 and 71 in a "debouncing" circuit. Otherwise, the counter within the block 77 could be incremented or decremented more than one count each time one of these buttons is pushed. The second feature of the circuitry 79 is to allow multiple increments of the counter within the block 77 by emitting a stream of pulses of several per second into the counter within the block 77 after one of the buttons 69 or 71 has been held down for more than one second. This provides the ability of the operator to skip fast to a particular pattern that is desired to be used in testing. The particular pattern that the counter within the block 77 is set is shown in a two digit display 73 provided in the hand control unit to inform the practitioner of which pattern will be lighted upon his or her depressing the test switch 67.

The digital output of the pattern address generator 77 is applied simultaneously to decoding circuits 81 and 83. The circuit 81 decodes a digital signal output of the generator 77 and drives lights connected to anyone of the 18 different patterns 0 through 18 at output lines 85. It will be noted that patterns 1 through 17 appear on the display board 11 and pattern "0" is the wand 27. That is, when the pattern "0" is selected, the light 33 of the wand 27 will be lighted for the selected duration upon pressing either the test switch 67 on the hand control unit or a remote test switch 31 on the wand. Each of the lights that are selectively energized at the output of the decoding and driving circuits 81 has one terminal connected to an appropriate output of that circuit and the other terminal connected to a line 85 that comes from a power supply 87. The voltage in the line 85 is controlled by the overall pattern brightness control 59 and it will thus be noted that the brightness of all of the lights can be adjusted to a given threshold by the control 59. The center light 51 is generally made of a color different than the pattern light so that the patient will have no doubt as to what he or she should be viewing during the test. The brightness of the center light 51 is independently controlled by the brightness control 57.

The decoding circuits 81 are enabled by the stream of pulses received in a line 89. These pulses come from a pulse synchronizer 91 which in turn is driven by a brightness pulse generator 93, to which the brightness selection switch 61 is operably and controllably connected, and a duration pulse generator 95, to which the duration switch 63 and test switch 67 are operably and controllably connected. The duration pulse generator 95 emits at an output line 97 a pulse of a duration controlled by the selection on the duration selection switch 63; that is, a duration of 0.25 seconds, 0.5 seconds, 1.0 second or continuous in this specific embodiment. The brightness pulse generator 93, on the other hand, emits in an output line 99 a continuous train of pulses whose duty cycle is varied in response to the control switch 61. The pulse synchronizer 91 receives the pulses in both of the lines 97 and 99 and emits in its output line 89 a string of pulses as presented to it in the line 99 but only for the duration of the longer pulse in the line 97. Thus, the brightness of the pattern lights connected to the output of the decoding and driving circuit 81 is dependent upon the duty cycle of the pulses in the line 89 that are derived from the pulse generator 97, and the duration that the pattern lights are energized is controlled by the length of the pulse and the output of the generator 95.

The decoding circuit 83 is provided in combination with a driving circuit 101 to give a one digit display 75 on the hand control unit of the number of lights (in this case 2, 3 or 4) which are lighted for each of the test patterns. This allows the practitioner to view the display 75 and know what the patient's response should be when asked how many lights he or she sees in a given pattern. The decoding circuit 83 receives a digital output of the counter in the pattern address generator 77 and decodes that digital signal, which is an indication of which pattern is to be displayed, for indication in the one digit display 75.

It will be noted from FIG. 1 that the front semitransparent plastic screen 45 is inscribed with concentric circular and radial lines. This is for the use of the practitioner in positioning the light 33 at the end of the wand 27 when that is utilized for testing the patient.

It will be understood that although the various aspects of the present invention have been described with respect to a preferred embodiment thereof that the invention is entitled to protection within the full scope of the apended claims.

We claim:

1. A visual field testing unit, comprising:
   a frame especially adapted for one side to be hung against a building wall;
   a flat semi-transparent tinted sheet held by said frame on an opposite side thereof, a front surface of said sheet being black matte finished,
   a plurality of substantially point light sources held by said frame in a spaced apart relationship over a two-dimensional area behind said semi-transparent sheet and characterized by being visible through said sheet when appropriately energized with electrical energy, said sheet attenuating enough light to make said lights normally invisible when they are not energized; and
   control means connected to each of said lights for selectively energizing in time sequence various pre-determined distinct combinations of only a few of said lights at one time, whereby blind spots in a person's visual field of view may be identified.

2. The visual field testing unit according to claim 1 wherein said control means comprises means including an electronic memory for automatically sequencing the energization of said various distinct combinations of lights through a pre-set sequence of light patterns.

3. The visual field testing unit according to claim 2 wherein said control means additionally comprises means including a first manually operated switch for initiating advance from one pre-determined distinct light pattern to a next in order.

4. The visual field testing unit according to claim 3 wherein said control means additionally comprises means responsive to said sequencing means for providing an indication of the particular one of said pre-determined light patterns that is being displayed.

5. The visual field testing unit according to claim 3 wherein said control means additionally comprises means including a second manually operated switch for initiating energization of a particular one of the predetermined distinct combination of lights at which the control means has been set in response to operation of said first switch.

6. The visual field testing unit according to claim 5 wherein said control means additionally comprises means for controlling the brightness of said light sources when energized.

7. The visual field testing unit according to claim 5 wherein said control means additionally comprises means responsive to a third manual switch setting for terminating the display after a duration of time established by said third switch setting.

8. The visual field testing unit according to claim 6 which additionally comprises a light wand having a single substantially point light source at one end thereof, said single light constituting one of said combinations of lights, whereby the light wand may be energized for a time set by said third switch upon actuation of said second switch.

9. The visual field testing unit according to claim 7 wherein said control means additionally comprises means responsive to said sequencing means for providing an indication of the number of lights of the most recent of said pre-determined light patterns that is energized.

10. The visual field testing unit according to claim 9 wherein each of said switches and indication means are packaged into a hand-held unit adapted for use a distance remote from said screen.

* * * * *